US009265446B1

(12) United States Patent
Bohler

(10) Patent No.: US 9,265,446 B1
(45) Date of Patent: Feb. 23, 2016

(54) BREATH TESTING SYSTEM

(76) Inventor: Elliott Bohler, Fayetteville, NC (US)

(*) Notice: Subject to any disclaimer, the term of this patent is extended or adjusted under 35 U.S.C. 154(b) by 723 days.

(21) Appl. No.: 13/547,860

(22) Filed: Jul. 12, 2012

Related U.S. Application Data

(60) Provisional application No. 61/507,404, filed on Jul. 13, 2011.

(51) Int. Cl.
A61B 5/097 (2006.01)
A61B 10/00 (2006.01)

(52) U.S. Cl.
CPC ............... A61B 5/097 (2013.01); A61B 10/007 (2013.01)

(58) Field of Classification Search
CPC ...... A61B 10/0051; A61B 5/097; A61B 5/08; A61B 5/082; A61B 10/007; A61B 10/0045
USPC .......................................... 600/530, 573–584
See application file for complete search history.

(56) References Cited

U.S. PATENT DOCUMENTS

| | | | |
|---|---|---|---|
| 1,525,631 A | 11/1923 | White | |
| 2,780,220 A | 11/1955 | Dyer, Jr. | |
| 3,507,269 A | 4/1970 | Berry | |
| 3,713,434 A | 1/1973 | Leslie, Jr. | |
| 4,525,342 A * | 6/1985 | Weiss et al. | 424/49 |
| 5,270,174 A | 12/1993 | Rosenberg | |
| 6,244,117 B1 * | 6/2001 | Mengel et al. | 73/863.21 |
| 6,264,615 B1 | 7/2001 | Diamond et al. | |
| 6,312,395 B1 * | 11/2001 | Tripp et al. | 600/572 |
| 7,413,550 B2 | 8/2008 | MacDonald et al. | |
| 7,582,485 B2 | 9/2009 | Boga et al. | |
| 2003/0100842 A1 | 5/2003 | Rosenberg et al. | |
| 2005/0085739 A1 * | 4/2005 | MacDonald et al. | 600/530 |

OTHER PUBLICATIONS http://www.wellstartrading.com/upload/productos/625/thumb/6. JPG, http://www.wellstartrading.com/productos/625 (see included PDF for reproduction of both pages).*
CNN 2011 article; http://www.cnn.com/2011/HEALTH/02/13/bad. breath.remedies/.*

* cited by examiner

Primary Examiner — Michael Kahelin
Assistant Examiner — Tho Tran
(74) Attorney, Agent, or Firm — Goldstein Law Offices, P.C.

(57) ABSTRACT

A breath tester and method for sampling the odor of an user's saliva. The tester includes an elongated testing surface having a closed end and an open end to collect the saliva. The user collects and traps the saliva on the elongated testing surface and smells the surface to self determine the presence of halitosis. In one embodiment, the tester has a handle mounted to one end of the elongated testing surface. The breath tester can be disposed in a hollow housing. The sampling of the saliva can be allowed to dry upon the elongated testing surface before smelling.

4 Claims, 3 Drawing Sheets

BREATH TESTING SYSTEM

CROSS-REFERENCE TO RELATED APPLICATIONS

This application is a nonprovisional utility application of the provisional patent application, Ser. No. 61/507,404 filed in the United States Patent Office on Jul. 13, 2011 and claims the priority thereof.

TECHNICAL FIELD

The present disclosure relates generally to a device to allow a user to test and smell their own breath. More specifically, the present invention relates to a testing surface that collects, traps and selectively dries saliva from a user for the user to smell and self-determine the presence of halitosis.

BACKGROUND

Halitosis, commonly known as bad breath, is a common concern for many people. The mouth and nasal passages are home to hundreds of bacterial species with various nutritional preferences. In otherwise healthy people, the very back of the tongue, rather than the teeth and gums, is the main source of bad breath. This region is poorly cleansed by saliva and contains numerous tiny invaginations in which bacteria can hide. Additional oral sources of bad breath include poor oral hygiene, gum inflammation, faulty dental work, unclean dentures and abscesses.

The detection and diagnosis of halitosis has traditionally involved self-monitoring which is typically accomplished by breathing into one's own hand and then sniffing the trapped contents or a person suspecting that they have halitosis can utilize another person to sample their breath and render a subjective diagnosis. However, this is an imprecise and potentially inconclusive method. A more exacting method of detecting halitosis is needed.

While these methods may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

It is an aspect of an example embodiment in the present disclosure to produce a device for allowing a user to assess the status of his or her own breath. Accordingly, the present disclosure describes a tester and methodology which allows a user to sample saliva from the mouth and use his or her own sense of smell to assess the status of the breath.

It is another aspect of an example embodiment in the present disclosure to produce a breath tester for sampling an user's saliva. The tester includes an elongated testing surface having a closed end and an open end to collect the saliva and a handle mounted to one end of the elongated testing surface.

It is further aspect of an example embodiment in the present disclosure to produce a breath tester for sampling an user's saliva. The tester further includes a testing surface to collect the saliva, a bottom cap secured to the testing surface, an elongated hollow housing open at a first end to receive the testing surface and bottom cap for storage, a closure cap to seal the first end of the housing, and a cord to attach the bottom cap and the closure cap.

It is yet another aspect of an example embodiment in the present disclosure to provide a method of collecting an user's saliva. The method includes collecting a sample of saliva in an elongated testing surface, allowing the saliva to dry upon the elongated testing surface, and smelling the elongated testing surface to determine one's breath.

The present disclosure describes a breath tester and method for sampling the odor of an user's saliva. The tester includes an elongated testing surface having a closed end and an open end to collect the saliva and a handle mounted to one end of the elongated testing surface. The breath tester can be disposed in a hollow housing. The sampling of the saliva can be allowed to dry upon the elongated testing surface, so that the user can smell the elongated testing surface to self-determine one's breath.

To the accomplishment of the above and related aspects of the disclosure may be embodied in the form illustrated in the accompanying drawings. Attention is called to the fact, however, that the drawings are illustrative only. Variations are contemplated as being part of the disclosure, limited only by the scope of the claims.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The structure, operation, and advantages of the present disclosure will become further apparent upon consideration of the following description taken in conjunction with the accompanying figures. The figures are intended to be illustrative, not limiting. Certain elements in some of the figures may be omitted, or illustrated not-to-scale, for illustrative clarity. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1:
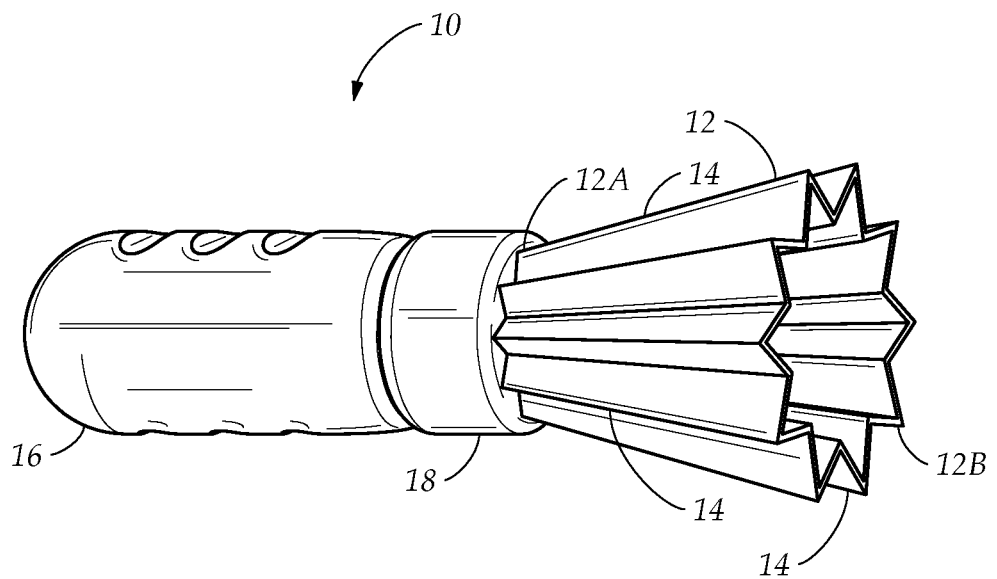
FIG. 1 is a diagrammatic perspective view of a breath tester, including a testing surface and handle, in accordance with the present disclosure.

The present disclosure describes a method of testing a user's breath using an apparatus illustrated in FIG. 1. In broad terms, the user collects saliva in a testing surface, allows the saliva to dry, and smells the testing surface. This alleviates the problem of uncertainty regarding the offensive odors of halitosis, allowing the user to self-determine the presence of offensive odors in the user's breath.

Referring to FIG. 1, a breath tester 10 is illustrated, designed to collect an user's saliva. Tester 10 has an elongated testing surface 12 that acts as a testing surface to collect the saliva. Testing surface 12 can be of any desired shape, such as a cone, funnel, or cup shaped. It is generally desirable, however, that the testing surface be generally formed as a container of sorts, having a closed end 12a, and an open end 12b. The testing surface 12 can be constructed of any suitable material, such as a plastic polymer or paper substrate. As illustrated, the elongated testing surface 12 has pleats 14 extending along the elongated testing surface, fully between the closed end 12a and open end 12b, so that the testing surface 12 selectively expands to a broader surface area after the saliva has been collected. This expansion provides more surface area for trapping and drying of the collected saliva. It is also within the terms of the embodiment for the elongated testing surface 12 to have perforations (not shown) through the material.

Further seen in FIG. 1 is a handle 16. Handle 16 is disposed adjacent to the closed end 12a of testing surface 12 and is secured to testing surface 12. Handle 16 is used to provide the user a way of holding and manipulating tester 10 when extracting saliva from the mouth, and later when smelling it. Testing surface 12 attaches to handle 16 in any suitable way, such as an adhesive. As shown, the testing surface 12 is ensconced within end portion 18 of handle 16.

Figure 2:
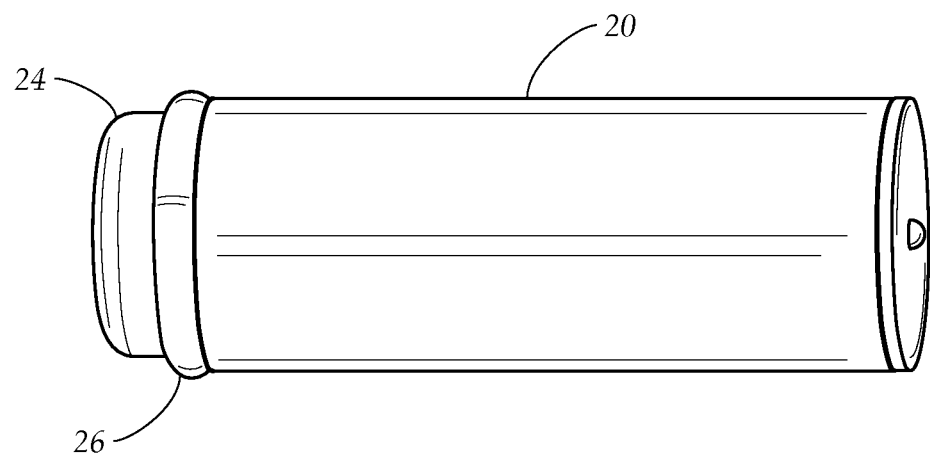
FIG. 2 is a diagrammatic perspective view of a housing storing the breath tester.

Referring to FIG. 2, there is illustrated a further embodiment incorporating a breath tester 21 disposed in a hollow housing 20 provided to store the device 21 (further described below) so that the breath tester can be conveniently carried for use as desired. Hollow housing 20 is typically a hollow cylinder constructed of any suitable material, such as, for example, a plastic polymer.

Figure 3:
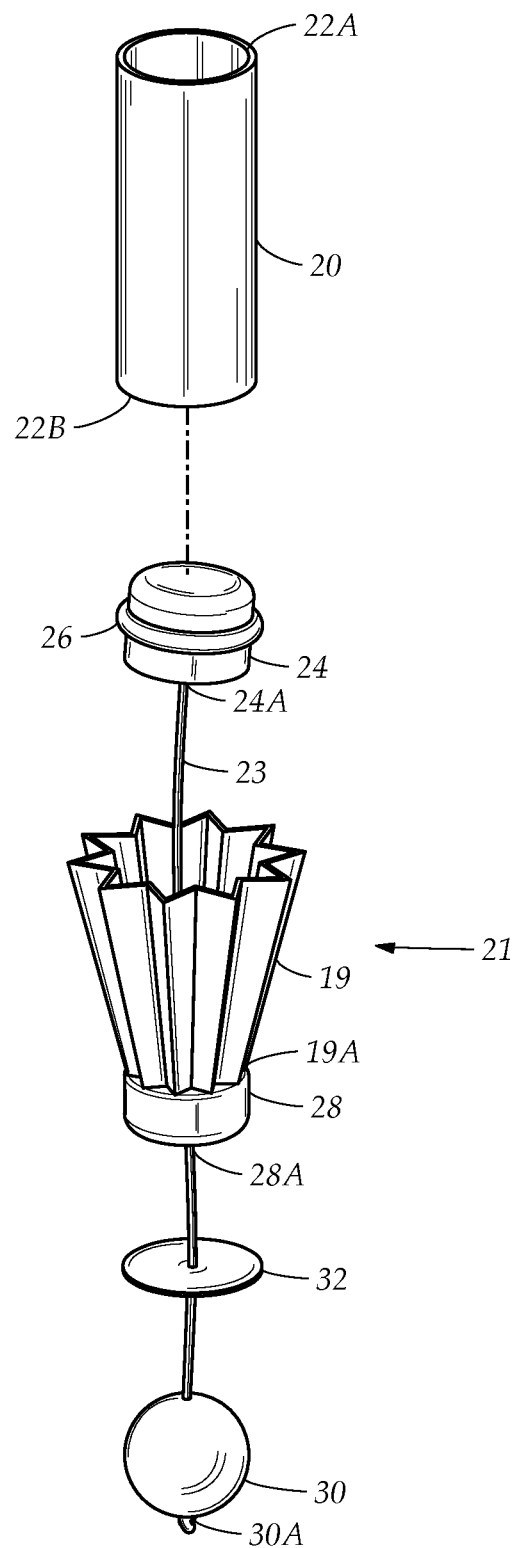
FIG. 3 is a diagrammatic perspective view of the breath tester and associated elements employed for storage.

Referring to FIG. 3, there is illustrated an exploded view of the housing 20 and the components of the breath tester 21 wherein the housing is used for storing a testing surface 19 (compare testing surface 12) therein. Hollow housing 20 is cylindrical with openings 22a and 22b on each end, respectively. Within the hollow housing 20 is disposed a breath testing assembly 21 connected along a cord 23 of material, such as an elastic band, including closure cap 24, testing surface 19, bottom cap 28, rear closure 32 and tension ball 30. Encircling closure cap 24 is lip 26, which secures closure cap 24 within first opening 22a, as shown in FIG. 2, until the user wishes to engage the tester 10. Testing surface 19 has the same shape and purpose as testing surface 12 described above and illustrated in FIG. 1. Bottom cap 28 is attached to the closed end 19a of testing surface 19 and acts support the testing surface, and attaches thereto by any suitable means, such as an adhesive. Tension ball 30 allows the testing surface 19 to advance out of the first end 22a of housing 20 when the user wishes to engage the tester 21, as discussed in more detail below. Rear closure 32 seals the second open end 22b of the housing 20.

A cord 23, which can be constructed of a line of elastic material, is attached to the rear portion 24a of closure cap 24 through suitable means, such as an adhesive. The cord 23 extends through the center of the testing surface 19 and through an opening 28a in the bottom cap 28. Further, cord 23 extends through an opening 30a in the tension ball 30, and is knotted behind opening 30a opposite to the side adjacent to the bottom cap 28. Finally, cord 23 is connected to rear closure 32, through any suitable means, such as an adhesive. Cord 23 is held in tension through the breath testing assembly 21, and preferably has some elasticity.

When the breath testing assembly 21 is assembled within housing 20, closure cap 24 extends outward from open first end 22a, as shown in FIG. 2, and testing surface 19 and bottom cap 28 are all lodged within housing 20, and rear closure 32 seals housing 20 and is lodged within second opening 22b until the user deploys tester 10, as described herein before. The tension ball 30 remains outside of the housing 20.

In order to utilize the breath testing assembly 21, the user holds the housing 20 with one hand and then pulls on closure cap 24 to disengage the lip 26 from the first end 22a of the housing 20. This pulling motion, which is counteracted by the knot behind opening 30a of the tension ball 30 causes the cord 23 to pull against the tension ball 30 which can then move in the direction of the bottom cap 28 so that the testing surface 19 moves out through opening 22a of the housing 20. The user then collects saliva in testing surface 19, and allow this saliva to dry. The user then smells the saliva to self-determine his breath. In a preferred embodiment, the user has the option of returning testing surface 19 into the housing 20 by allowing the resilient cord 23 to pull the testing surface 19 back into housing 20 until the closure cap 24 is back in place as shown in FIG. 2, for further storage While the apparatus has been disclosed with regards to testing for halitosis, it is also within the terms of the disclosure that the material forming the testing surface may have chemicals upon it to detect alcohol or another chemical. In one embodiment, the testing surface has a substrate that changes color.

It is understood that when an element is referred hereinabove as being "on" or "adjacent to" another element, it can be directly on or adjacent to the other element or intervening elements may be present therebetween. In contrast, when an element is referred to as being "directly on" or "directly adjacent to" another element, there are no intervening elements present.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

In the description hereinabove, numerous details are set forth in order to provide a thorough understanding of the present disclosure. It will be appreciated by those skilled in the art that variations of these specific details are possible while still achieving the results of the present disclosure. Well-known processing steps are generally not described in detail in order to avoid unnecessarily obfuscating the description of the present disclosure.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a system for allowing a user to sample the odor or his or her own saliva to ascertain the status of the breath. The disclosure is illustrated by example in the drawing figures, and throughout the written description. It should be understood that numerous variations are possible, while adhering to the inventive concept. Such variations are contemplated as being a part of the present disclosure.

What is claimed is:

1. A breath tester for a user to self-determine the presence of halitosis in a user's mouth having saliva, comprising:
   an elongated testing surface formed into a container for collecting, trapping and drying the user's saliva, the elongated testing surface having a closed end and an open end, the elongated testing surface having pleats extending along the elongated testing surface, fully between the closed end and the open end of the elongated testing surface, the elongated testing surface having a surface area, the elongated testing surface expanding the pleats thereby expanding the surface area, the elongated testing surface enabling the user to smell the saliva trapped within the pleats to self-determine the presence of halitosis;
   a housing for selectively holding the elongated testing surface, the housing having a pair of openings, a first opening and a second opening, at least one opening for moving the elongated testing surface out of the housing;
   a breath testing assembly disposed within the housing, the breath testing assembly having a closure cap for closing the first opening of the housing, a rear closure for closing the second opening of the housing, a bottom cap operably coupled to the closed end of the elongated testing surface, the rear closure and a tension ball elastically connected by a cord having a pair of ends, a first end attaching to the closure cap, the second end extending through the container formed by the testing surface, further extending through the bottom cap on the closed end of the testing surface, further extending through the rear closure and passing through the tension ball, the cord secured by a knot on the second end after passing through the ball.

2. The breath tester as described in claim 1, wherein the closure cap has a lip that secures the closure cap within the first opening of the housing.

3. A method for self-determining the presence of halitosis by a user having a mouth with saliva, using a breath tester having a housing the housing including a first opening and a second opening, the housing containing an elongated testing surface formed into a container having a closed end and an open end, the elongated testing surface having pleats fully extending along the elongated testing surface between the ends, the housing having a closure cap on the first opening extending outward from the open end of the elongated testing surface, a bottom cap adjacent to the closed end of the elongated testing surface, and a rear closure adjacent to the bottom cap, the rear closure sealing the second opening of the housing and a tension ball adjacent to the rear closure, the tension ball, the rear closure, the bottom cap, the closure cap connected by a cord extending through the open end and closed end of the elongated testing surface, comprising:
   disengaging the closure cap and pulling on the tension ball to move the bottom cap toward the first opening, thereby pushing the elongated testing surface out through the first opening of the housing;
   collecting saliva from the mouth onto the container formed by the elongated testing surface;
   drying the collected saliva;
   expanding the pleats of the elongated testing surface, thereby increasing an area of the elongated testing surface to promote drying; and
   smelling the saliva on the elongated testing surface to self-determine if halitosis is present.

4. The method for self-determining the presence of halitosis as described in claim 3, wherein the step of smelling the dried saliva on the elongated testing surface is followed by the step of pulling the tension ball away from the rear closure, thereby pulling the elongated testing surface into the housing through the first opening.

* * * * *